US00PP27112P2

(12) United States Plant Patent
Meinl

(10) Patent No.: US PP27,112 P2
(45) Date of Patent: Aug. 30, 2016

(54) ***HYDRANGEA* PLANT NAMED 'SAXWHIMAR'**

(50) Latin Name: *Hydrangea macrophylla*
Varietal Denomination: Saxwhimar

(71) Applicant: Katrin Meinl, Dresden (DE)

(72) Inventor: Katrin Meinl, Dresden (DE)

(73) Assignee: Kühne Jungpflanzen Claus + Torsten Kühne GbR, Dresden (DE)

( * ) Notice: Subject to any disclaimer, the term of this patent is extended or adjusted under 35 U.S.C. 154(b) by 92 days.

(21) Appl. No.: 14/121,803

(22) Filed: Oct. 20, 2014

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — June Hwu
(74) *Attorney, Agent, or Firm* — C. A. Whealy

(57) ABSTRACT

A new and distinct cultivar of *Hydrangea* plant named 'Saxwhimar', characterized by its upright and mounded plant habit; moderately vigorous growth habit; strong stems; and large mophead-type inflorescences that when treated with aluminum sulfate produce violet blue-colored sterile flowers with light blue-colored margins.

2 Drawing Sheets

Botanical designation: *Hydrangea macrophylla.*
Cultivar denomination: 'SAXWHIMAR'.

BACKGROUND OF THE INVENTION

The present invention relates to a new and distinct cultivar of *Hydrangea* plant, botanically known as *Hydrangea macrophylla* and hereinafter referred to by the name 'Saxwhimar'.

The new *Hydrangea* plant is a product of a planned breeding program conducted by the Inventor in Dresden, Germany. The objective of the breeding program was to develop new container-type *Hydrangea* plants with strong stems, early flowering response and attractive leaf, stem and flower coloration.

The new *Hydrangea* plant originated from a cross-pollination in 2009 of *Hydrangea macrophylla* 'Horpill', disclosed in U.S. Plant Pat. No. 19,761, as the female, or seed, parent with an unidentified proprietary selection of *Hydrangea macrophylla*, not patented, as the male, or pollen, plant. The new *Hydrangea* plant was discovered and selected by the Inventor in 2011 as a flowering plant from within the progeny of the stated cross-pollination in a controlled greenhouse environment in Dresden, Germany.

Asexual reproduction of the new cultivar by softwood cuttings in Dresden, Germany since June, 2011 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Saxwhimar'.

These characteristics in combination distinguish 'Saxwhimar' as a new and distinct *Hydrangea* plant:

1. Upright and mounded plant habit.
2. Moderately vigorous growth habit.
3. Strong stems.
4. Large mophead-type inflorescences that when treated with aluminum sulfate produce violet blue-colored sterile flowers with light blue-colored margins.

Plants of the new *Hydrangea* differ primarily from plants of the female parent, 'Horpill', in the following characteristics:

1. Plants of the new *Hydrangea* are larger than and not as compact as plants of 'Horpill'.
2. Plants of the new *Hydrangea* are more freely branching than plants of 'Horpill'.
3. When treated with aluminum sulfate, plants of the new *Hydrangea* and 'Horpill' differ in sterile flower color as plants of 'Horpill' produce violet-colored sterile flowers with lighter violet-colored margins.

Plants of the new *Hydrangea* differ primarily from plants of the male parent selection in plant habit as plants of the new *Hydrangea* are more compact and uniform than plants of the male parent selection.

Plants of the new *Hydrangea* can be compared to plants of *Hydrangea macrophylla* 'Bavaria', not patented. Plants of the new *Hydrangea* differ primarily from plants of 'Bavaria' in the following characteristics:

1. Plants of the *Hydrangea* have stronger stems than plants of 'Bavaria'.
2. Plants of the new *Hydrangea* have smaller inflorescences than plants of 'Bavaria'.
3. When treated with aluminum sulfate, sterile flowers of plants of the new *Hydrangea* have narrower lighter-colored margins than sterile flowers of plants of 'Bavaria'.
4. Plants of the new *Hydrangea* are more high temperature tolerant than plants of 'Bavaria'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'Saxwhimar' grown in a container.

The photograph on the second sheet is a close-up view of typical inflorescences of 'Saxwhimar'.

DETAILED BOTANICAL DESCRIPTION

Plants used in the aforementioned photographs and in the following description were grown during the spring in 3-liter containers in a glass-covered greenhouse in Dresden, Germany and under cultural practices typical of commercial *Hydrangea* production. Plants of the new *Hydrangea* were two years old when the photographs and description were taken. During the production of the plants, day temperatures ranged from 18° C. to 25° C. and night temperatures ranged from 16° C. to 17° C. Plants used for the description and photographs were treated with aluminum sulfate to "blue" the inflorescences. In the following description, color references are made to The Royal Horticultural Society Colour Chart, 2007 Edition, except where general terms of ordinary dictionary significance are used.

Botanical description: *Hydrangea macrophylla* 'Saxwhimar'.

Parentage:

*Female, or seed, parent.*—*Hydrangea macrophylla* 'Horpill', disclosed in U.S. Plant Pat. No. 19,761.

*Male, or pollen, parent.*—Unidentified proprietary selection of *Hydrangea macrophylla*, not patented.

Propagation:

*Type cutting.*—By softwood cuttings.

*Time to initiate roots, summer.*—About 17 days at temperatures about 18° C.

*Time to initiate roots, winter.*—About 19 days at temperatures about 18° C.

*Time to produce a rooted young plant, summer.*—About 30 days at temperatures about 18° C.

*Time to produce a rooted young plant, winter.*—About 32 days at temperatures about 18° C.

*Root description.*—Fine, fibrous; white to grey in color.

*Rooting habit.*—Moderately freely branching; sparse.

Plant description:

*Plant and growth habit.*—Perennial subshrub; upright and mounded plant habit; broadly inverted triangle; freely branching habit with about 14 lateral branches developing per plant; strong lateral branches; moderately vigorous growth habit.

*Plant height.*—About 38 cm.

*Plant diameter or area of spread.*—About 55.8 cm.

*Lateral branches.*—Length: About 19.9 cm. Diameter: About 6 mm. Internode length: About 5.1 cm. Texture: Smooth, glabrous. Strength: Strong. Aspect: About 40° from vertical. Color, developing: Close to 144A; at the nodes, slightly tinged with close to N186C. Color, developed: Close to 199C to 199D. Lenticels: Density: Sparse to medium density. Length: About 2 mm. Diameter: About 0.75 mm. Color: Close to N186C.

Leaf description:

*Arrangement.*—Opposite, simple.

*Length.*—About 12.6 cm.

*Width.*—About 9.1 cm.

*Shape.*—Ovate to broadly ovate.

*Apex.*—Broadly apiculate to cuspidate.

*Base.*—Short attenuate.

*Margin.*—Serrate.

*Texture, upper and lower surfaces.*—Glabrous; slightly rugose.

*Venation pattern.*—Pinnate.

*Color.*—Developing leaves, upper surface: Close to 137B and N137B. Developing leaves, lower surface: Close to between 138B and 147B. Fully expanded leaves, upper surface: Darker than between N137A and 147A; venation, close to 144A. Fully expanded leaves, lower surface: Close 137B; venation, close to 144A to 144B.

*Petioles.*—Length: About 2.5 cm. Diameter: About 3 mm. Texture, upper and lower surfaces: Smooth, glabrous. Color, upper and lower surfaces: Close to 144A.

Inflorescence & flower description:

*Flower type and habit.*—Showy single sterile and inconspicuous single fertile flowers arranged on terminal mophead-type panicles; panicles flattened globular in overall shape; fertile flowers face mostly upright and sterile flowers face upright to outwardly.

*Fragrance.*—Moderately faint; pleasant.

*Natural flowering season.*—Continuous flowering from late spring to late summer in Germany.

*Flower longevity, fertile flowers.*—Flowers last about one week on the plant; fertile flowers not persistent.

*Flower longevity, sterile flowers.*—Flowers last about six weeks on the plant; sterile flowers persistent.

*Quantity of flowers.*—Freely flowering; about 20 fertile flowers and about 125 sterile flowers per panicle.

*Panicle height.*—About 11.8 cm.

*Panicle diameter.*—About 18.2 cm.

*Flower diameter, fertile flowers.*—About 1.2 cm.

*Flower depth (height), fertile flowers.*—About 7 mm.

*Flower diameter, sterile flowers.*—About 4.9 cm.

*Flower depth (height), sterile flowers.*—About 1.7 cm.

*Flower buds, fertile flowers.*—Length: About 4 mm. Diameter: About 4 mm. Shape: Globular. Color: Close to 136D.

*Flower buds, sterile flowers.*—Length: About 9 mm. Diameter: About 8 mm. Shape: Ovoid. Color: Close to 145B.

*Petals, fertile flowers only.*—Quantity and arrangement: Five in a single whorl. Length: About 4.5 mm. Width: About 2 mm. Shape: Ovate, concave. Apex: Acute. Base: Cuneate. Margin: Entire. Texture, upper and lower surfaces: Smooth, glabrous. Color: When opening and fully opened, upper surface: Close to 96B; color does not change with development. When opening and fully opened, lower surface: Close to 95C; color does not change with development.

*Sepals, fertile flowers.*—Quantity and arrangement: Five in a single whorl. Length: About 1 mm. Width: About 0.1 mm. Shape: Deltoid. Apex: Acute. Base: Broadly cuneate. Margin: Entire. Texture, upper and lower surfaces: Smooth, glabrous. Color: When opening, upper and lower surfaces: Close to 145B to 145C; apices flushed with close to 98C to 98D. Fully opened, upper and lower surfaces: Close to 145B to 145C; apices flushed with close to 98C to 98D; color does not change with development.

*Sepals, sterile flowers*.—Quantity and arrangement: Four or occasionally five in a single whorl. Length: About 2.9 cm. Width: About 3 cm. Shape: Broadly ovate to deltoid. Apex: Broadly and bluntly acute. Base: Broadly cuneate. Margin: Entire. Texture, upper and lower surfaces: Smooth, glabrous. Color: When opening, upper surface: Close to 93B to 93C. When opening, lower surface: Close to 90D; towards the base, tinged with close to 150D. Fully opened, upper surface: Close to 96A and fading towards the margins to close to 100D and 101D; with development, main color becomes closer to 96A flushed with close to 93B. Fully opened, lower surface: Close to between 96D and 97A and fading towards the margins to close to 100D and 101D; with development, main color becoming closer to between 92A and 94C.

*Pedicels, fertile flowers*.—Angle: About 30° from vertical. Strength: Moderately strong. Length: About 5 mm. Diameter: About 1 mm. Texture: Smooth, glabrous. Color: Close to 102D.

*Pedicels, sterile flowers*.—Angle: About 30° from lateral branch. Strength: Strong. Length: About 2 cm. Diameter: About 1.5 mm. Texture: Smooth, glabrous. Color: Close to 94B; towards the base, tinged with close to 70B.

*Reproductive organs, fertile flowers*.—Stamens: Quantity per flower: About eight. Filament length: About 3 mm. Filament color: Close to N155A. Anther length: About 1 mm. Anther shape: Broadly reniform. Anther color: Close to 116A to 116B. Pollen amount: Moderate to abundant. Pollen color: Close to 156D. Pistils: Pistil quantity per flower: About three. Pistil length: About 2 mm. Stigma shape: Club-shaped. Stigma color: Close to 145D. Style length: About 1.5 mm. Style color: Close to 122D. Ovary color: Close to 155A.

*Reproductive organs, sterile flowers*.—Stamens: Quantity per flower: About eight. Filament length: About 2 mm. Filament color: Close to N155A. Anther length: About 1 mm. Anther shape: Broadly reniform. Anther color: Close to 116A to 116B. Pollen amount: Moderate to abundant. Pollen color: Close to 156D. Pistils: Pistil quantity per flower: About two. Pistil length: About 1.5 mm. Stigma shape: Club-shaped. Stigma color: Close to 155A. Style length: About 1 mm. Style color: Close to 157D. Ovary color: Close to 157D.

*Seeds and fruits*.—To date, seed and fruit development have not been observed on plants of the new *Hydrangea*.

Disease & pest resistance: Plants of the new *Hydrangea* have not been observed to be resistant to pathogens and pests common to *Hydrangea* plants.

Temperature tolerance: Plants of the new *Hydrangea* have been shown to be tolerant to temperatures in USDA Hardiness Zones 5 to 9.

It is claimed:

1. A new and distinct *Hydrangea* plant named 'Saxwhimar' as illustrated and described.

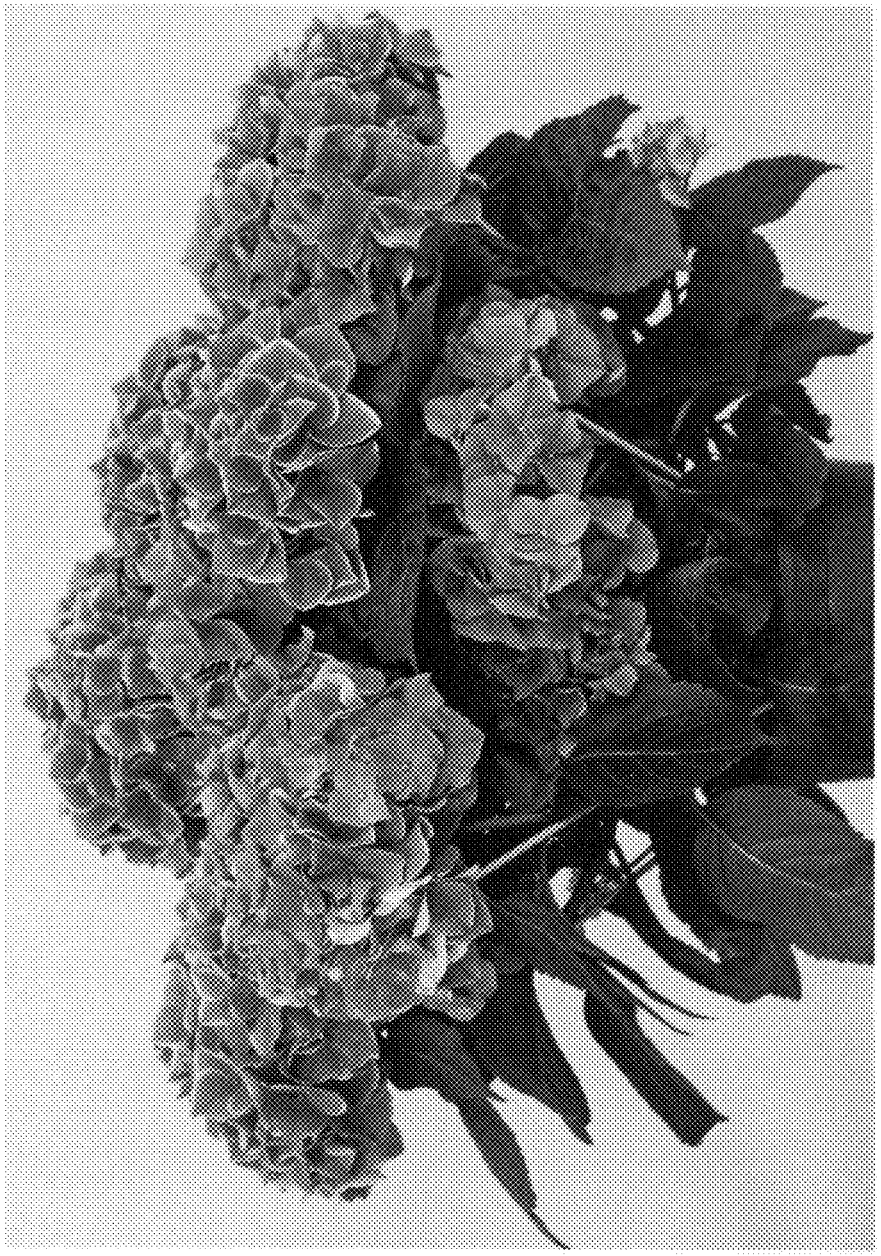

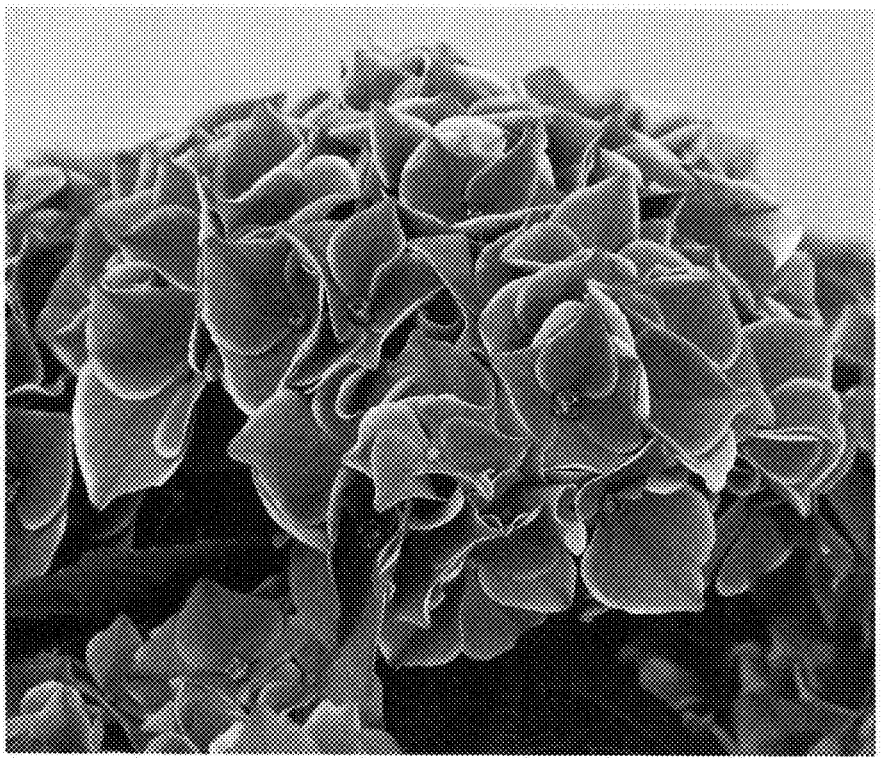

* * * * *